United States Patent [19]

Lee

[11] Patent Number: 5,212,172

[45] Date of Patent: May 18, 1993

[54] 4-(1-HYDROXY-2-SUBSTITUTED AMINO)ETHYL-5-HYDROXY-2(5H)-FURANONES AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 792,977

[22] Filed: Nov. 15, 1991

Related U.S. Application Data

[62] Division of Ser. No. 493,895, Mar. 15, 1990, Pat. No. 5,081,147.

[51] Int. Cl.$^5$ .............. A61K 31/495; A61K 31/535; C07D 405/12; C07D 413/12
[52] U.S. Cl. ..................... 514/231.5; 514/252; 544/152; 544/379
[58] Field of Search .................. 544/152, 379; 514/231.5, 252

[56] References Cited

U.S. PATENT DOCUMENTS 5,081,261  1/1992  Lee ...................... 544/379

Primary Examiner—Robert W. Ramsuer
Attorney, Agent, or Firm—Gabor L. Szekeres; Martin A. Voet; Robert J. Baran

[57] ABSTRACT

Compounds of the formula

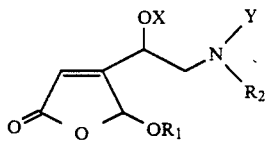

Formula 1 where
$R_1$ is H or alkyl of 1 to 20 carbons, $CO-R_1^*$, $CO-O-R_1^*$, $CO-NH-R_1^*$, or $PO(OR_1^*)_2$, $PO(OR_1^*)R_1^*$ where $R_1^*$ independently is H, alkyl of 1 to 20 carbons, phenyl, or substituted phenyl;

$R_2$ is H or alkyl of 1 to 20 carbons;

X is H, $R_3$, $CO-R_3$, $CO-O-R_3$, $CO-NH-R_3$, $CO-N-(R_3)_2$, $PO(OR_3)_2$, $PO(OR_3)R_3$, and $R_3$ independently is H, phenyl, substituted phenyl, alkyl of 1 to 20 carbons or is alkyl of 1 to 20 carbons substituted with a hydroxyl, alkoxy, substituted amino, thioalkoxy or with a $COR_3^*$ group where $R_3^*$ is H, lower alkyl, OH, $OR_3^{}$, $NH_2$, $NHR_3^{}$ or $N(R_3^{})_2$ group where $R_3^{}$ independently is H or lower alkyl, with the proviso that when X is $CO-O-R_3$ or is $CO-NH-R_3$ then $R_3$ is not hydrogen;

Y is H, $R_4$, $CO-R_4$, $CO-O-R_4$, CO-N-piperazinyl, CO-N-substituted N-piperazinyl, CO-N-morpholinyl, CO-N-substitutetd N-morpholinyl, $CO-NH-R_4$, or $CO-N(R_4)_2$, $PO(OR_4)_2$, $PO(OR_4)R_4$, $SO_2OR_4$, or $SO_2R_4$, where $R_4$ independently is H, phenyl or substituted phenyl, or alkyl of 1 to 20 carbons, or is alkyl of 1 to 20 carbons substituted with a hydroxyl, alkoxy, substituted amino, thioalkoxy, with a $COR_4^*$ or with a $O-COR_4^*$group where $R_4^*$ is H, lower alkyl, OH, $OR_4^{}$, $NH_2$, $NHR_4^{}$ or $N(R_4^{})_2$ group where $R_4^{}$ is lower alkyl with the proviso that when Y is $CO-O-R_4$ then $R_4$ is not hydrogen, are disclosed. The compounds have anti-inflammatory activity in mammals, including humans.

13 Claims, No Drawings

4-(1-HYDROXY-2-SUBSTITUTED AMINO)ETHYL-5-HYDROXY-2(5H)-FURANONES AS ANTI-INFLAMMATORY AGENTS

1. CROSS-REFERENCE TO RELATED APPLICATION

The present application is a divisional of application Ser. No. 493,895 filed on Mar. 15, 1990, which has matured into U.S. Pat. No. 5,081,147.

BACKGROUND OF THE INVENTION

2. Field of the Invention

The present invention is directed to novel 4-(1-hydroxy-2-substituted amino)ethyl-5-hydroxy-2(5H)-furanones which are active as anti-inflammatory agents. The present invention is also directed to pharmaceutical compositions which comprise one or more of the novel compounds of the invention, to the methods of using these pharmaceutical compositions, and to the chemical processes of making the novel compounds.

3. Brief Description of the Prior Art

Manoalide is a compound isolated from a marine sponge [E. D. de Silva et al., *Tetrahedron Letters* 21:1611–1614 (1980)] which has anti-inflammatory, immunosuppressive and analgesic properties. Manoalide (Compound 1) the structure of which is shown below, includes a 5-hydroxy-2(5H)-furanone moiety, attached in the 4-position of the furanone ring to the rest of the molecule. Certain analogs of manolide, such as seco-manoalide (Compound 2) and dehydro-seco-manoalide (compound 3) also have antiinflammatory activity. For further description of the biological activity of manoalide and some of its derivatives reference is made to U.S. Pat. No. 4,447,445 and to European Patent Application No. 0133376 (published on February 20, 1985).

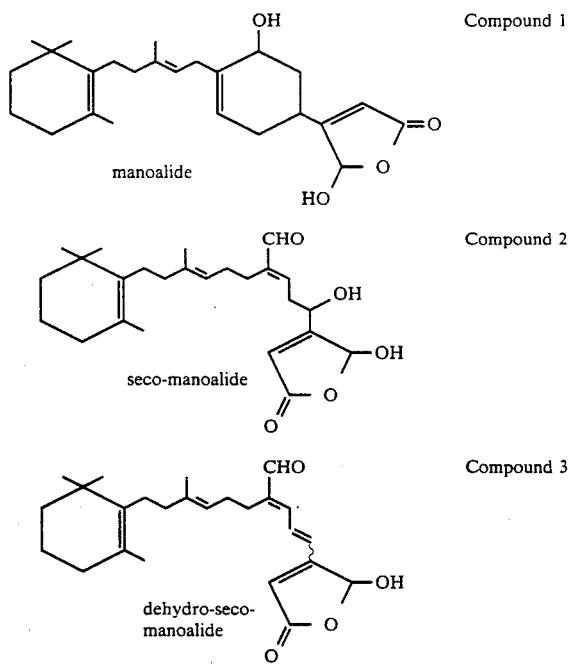

Synthetic analogs of of manoalide, particularly analogs having various substituents on the furanone moiety of manoalide, are described in several applications for United States Letters Patent by the same inventor as in the present application, the following of which have been allowed and are expected to issue as United States Letters Patent:

Ser. No. 259,225 filed on Oct. 18, 1988;
Ser. No. 281,126 filed on Dec. 7, 1988.

Published European Patent Application No. 0 295 056 discloses 4-substituted 5-hydroxy-2(5H)-furanones having antiinflammatory, immunosuppressive and antiproliferative activity where the substituents in the 4 position are a variety 1-hydroxyalkyl, 1-acyloxy-alkyl and 1-carbamoyloxy-alkyl groups.

SUMMARY OF THE INVENTION

The present invention covers compounds of Formula 1

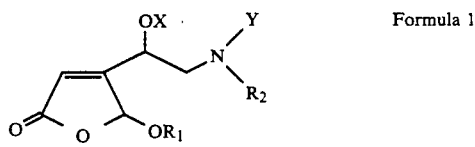

where $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is H, alkyl of 1 to 20 carbons, phenyl, or substituted phenyl;

$R_2$ is H or alkyl of 1 to 20 carbons;

X is H, $R_3$, $CO-R_3$, $CO-O-R_3$, $CO-NH-R_3$, $CO-N-(R_3)_2$, $PO(OR_3)_2$ or $PO(OR_3)R_3$, and $R_3$ independently is H, phenyl, substituted phenyl, alkyl of 1 to 20 carbons or is alkyl of 1 to 20 carbons substituted with a hydroxyl, alkoxy, substituted amino, thioalkoxy or with a $COR_3^*$ group where $R_3^*$ is H, lower alkyl, OH, $OR_3^{}$, $NH_2$, $NHR_3^{}$ or $N(R_3^{})_2$ group where $R_3^{}$ independently is H or lower alkyl, with the proviso that when X is $CO-O-R_3$ or is $CO-NH-R_3$ then $R_3$ is not hydrogen;

Y is H, $R_4$, $CO-R_4$, $CO-O-R_4$, CO-N-piperazinyl, CO-N-substituted N-perazinyl, CO-N-morpholinyl, CO-N-substitutetd N-morpholinyl, $CO-NH-R_4$, or $CO-N(R_4)_2$ $PO(OR_4)_2$ $PO(OR_4)R_4$, $SO_2OR_4$, or $SO_2R_4$, where $R_4$ independently is H, phenyl or substituted phenyl, or alkyl of 1 to 20 carbons, or is alkyl of 1 to 20 carbons substituted with a hydroxyl, alkoxy, substituted amino, thioalkoxy, with a $COR_4^*$ or with a $O-COR_4^*$ group where $R_4^*$ is H, lower alkyl, OH, $OR_4^{}$, $NH_2$, $NHR_4^{}$ or $N(R_4^{})_2$ group where $R_4^{}$ is lower alkyl with the proviso that when Y is $CO-O-R_4$ then $R_4$ is not hydrogen. The present invention also covers salts of the above-defined compounds, formed with pharmaceutically acceptable acids or bases, as applicable.

In a second aspect the present invention relates to pharmaceutical formulations comprising one or more compounds of Formula 1 (or pharmaceutically acceptable salts therof) in admixture with a pharmaceutically acceptable excipient, for the purpose of treating certain conditions, syndromes or diseases in mammals, including humans. The compounds of the invention have antiinflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

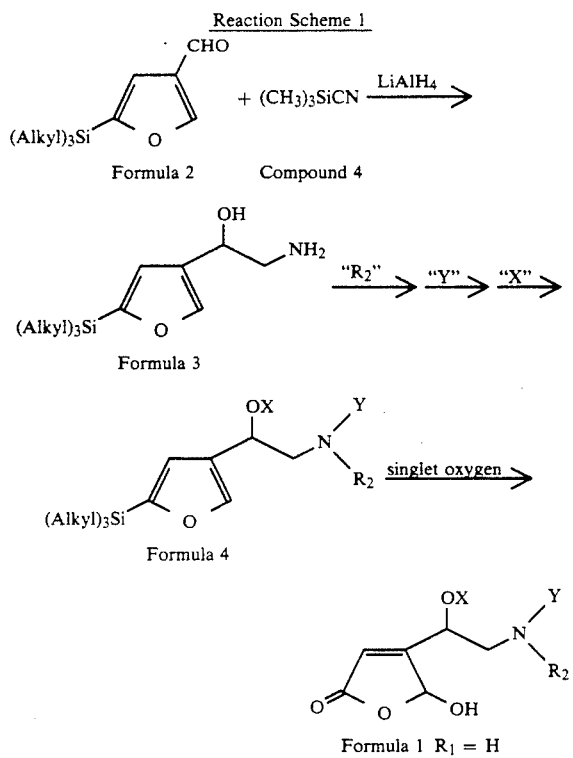

In still another aspect, the present invention relates to process of making the compounds of Formula 1, which process, shown in general terms on Reaction scheme 1, involves the reaction of a 5-trialkylsilyl-3-furaldehyde (Formula 2, "alkyl" has 1 to 10 carbons) with a trialkylsilyl cyanide (such as trimethylsilyl cyanide (Compound 4) to yield, after reduction with a hydride reagent (such as lithium aluminum hydride) a 4-(2-amino-1-hydroxy)ethyl-2-trialkylsilylfuran (Formula 3). The 4-(2-amino-1- hydroxy)ethyl-2-trialkylsilylfuran (Formula 3) derivatives are then reacted with appropriate reagents in one or more reaction steps to introduce the X and Y (and optionally $R_2$) substituents as applicable, respectively (X and Y having been defined in connection with Formula 1) into the vicinal hydroxy and amino functions of the side chain of the 2-trialkylsilylfuran molecule. The resulting X and Y substituted 4-(2-amino-1-hydroxy)ethyl-2-trialkylsilylfuran (Formula 4) is reacted with "singlet oxygen" to provide the compounds of Formula 1, where $R_1$ is hydrogen. When it is desirable to substitute (acylate, alkylate or the like) the 5-hydroxy function of the compounds of Formula 1, an $R_1$ group (as defined in connection with Formula 1) can be introduced into the 5-hydroxy-2(5H)-furanone compound by conventional means.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

The compounds of the invention contain a chiral center at the alpha carbon in the side chain on the 4-position of the furan ring. Certain compounds of the invention may contain one or more additional chiral centers. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1 or other ratios. Alternatively, each diastereomeric compound may be sterically and optically pure. However, all of the abovenoted forms, including optically pure enantiomers and mixtures thereof as well as all diastereomers are within scope of the present invention.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and with respect to the 5-position of the furanone moiety, those where the substituent is hydroxy or acetoxy ($R_1$ is H or $CH_3CO$).

With respect to the nitrogen on the beta carbon in the side chain (in the 4-position) of the furanone moiety, the preferred compounds of the invention are those where $R_2$ is hydrogen.

With respect to the alpha hydroxyl function in the side chain (in the 4-position) of the furan moiety, preferred compounds are where: the hydroxyl is unsubstituted (X=H), is esterified with an acid having the structure $R_3$—COOH, ($R_3$ is defined as for Formula 1), the hydroxyl is converted into a carbonate (X=CO—O—$R_3$) or carbamate (X=CO—NH—$R_3$). Particularly preferred in regard to this alpha hydroxyl function are acetate and propionate esters (X=COCH$_3$ or X=COCH$_2$CH$_3$), esters of long chain fatty acids such as dodecanoic acid (X=CO(CH$_2$)$_{10}$CH$_3$), esters of alpha-omega dicarboxylic acids, such as glutaric acid, or esters of long chain dicarboxylic acids (e.g. X=CO(CH$_2$)$_3$COOH or (X=CO(CH$_2$)$_{10}$COOH), carbonates where X=CO—O—$R_3$ and $R_3$ is alkyl, especially ethyl, carbamates where X=CO—NH—$R_3$ and $R_3$ is phenyl or alkyl.

With respect to the amino function in the side chain (in the 4-position) of the furan moiety, (Formula 1) preferred compounds are: alkyl sulfonamides (Y=SO$_2$R$_4$) particularly where the alkyl group (R$_4$) is methyl or alkyl of 6 to 20 carbons; carboxamides (Y=CO—R$_4$) formed from alkanoic acids, dialkylamino-substituted carboxamides derived from omega dialkylamino-substituted alkanoic acids (Y=CO—R$_4$ and R$_4$ is, for example, (CH$_3$)$_2$N(CH$_2$)$_3$), carboxamides derived from benzoic acid or substituted benzoic acid, including carboxamides derived from carboxy substituted benzoic acids (e.g. Y=CO—R$_4$ and R$_4$ is C$_6$H$_3$(COOH)$_2$), carboxamides derived from alpha-omega dicarboxylic acids (Y=CO—(CH$_2$)$_n$COOH, for example n is 3 or 10); alkyl phosphonates particularly where Y is PO-(OR$_4$)R$_4$ (R$_4$ is alkyl, particularly lower alkyl); alkyl carbamates (Y=CO—O—R$_4$) particularly where the alkyl group R$_4$ has 6 to 20 carbons); and urea derivatives (Y=CO—NH—R$_4$ or Y=CO—N—(R$_4$)$_2$) particularly in the former case where R$_4$ is alkyl of 6 to 20 carbons, or in the latter case R$_4$ is ethyl. Also preferred are urea derivatives where Y is CO-N-methylpiperazinyl, methylsulfon-substituted N-piperazinyl, or N-morpholinyl group.

The most preferred compounds of the invention, and specific routes to their syntheses are disclosed in the ensuing specific examples.

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase A2 in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility.

Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, GH$_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or Cl$^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40–94 |
| Mineral oil | 5–20 |
| Glycol solvent | 1–15 |
| Surfactant | 0–10 |
| Stabilizer | 0–10 |
| Active ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2 The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5–10 min trypsin-EDTA treatment whereas $GH_3$ cells were treated 2 to 5 min with a 1% pancreatin solution. Cells were immediately washed twice in a 20mM HEPES buffer (pH 7.4) containing 120mM NaCl, 6 mM KCl, 1 mM $MgSO_4$, 1 mg/ml glucose and 1 mg/ml pyruvate and 1.4mM calcium (medium A). Approximately $5 \times 10^6$ cells were suspended in medium A and incubated with 4uM fura-2AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340nm and emission wavelength set at 500nm. The cell suspension was continually stirred, maintained at 37° C. and equilibrated for approximately 5 min before addition of various agents. $[Ca^{2+}]i$ was calculated using the following formula:

$$[Ca^{2+}]_i = 220 \times \frac{F - Fmin}{Fmax - F}$$

All fluorescence values were measured relative to a EGTA-quenched signal determined as follows: F was the relative fluorescence measurement of the sample. $F_{max}$ was determined by lysing the cells with digitonin (100ug/ml) in DMSO. After $F_{max}$ was determined the pH was adjusted to 8, with NaOH and $Ca^{2+}$ chelated with 3mM EGTA to totally quench the fura-2 signal and obtain $F_{min}$.

When quin-2- was used, cells were incubated with 10uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., Clin Pharmacol Ther (1974) 16:900–904].

Inhibition of Phospholipase $A_2$

The effect of compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.
b. 1 36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5 M $H_2SO_4$ (40:10:1; v:v:v:).
f. 2 0 ml n-heptane and 1.0 ml H20 added; mixture centrifuged.
g. 2.0 ml n-heptane removed and treated with 200–300 mg of silica gel HR60.
h. Samples centrifuged; 1 ml of n-heptane SN removed and added to 10 ml scintillation fluid.
i. Samples counted on a scintillation counter.

Inhibition of Phosphoinositide-specific Phospholipase C

The effect of compounds of this invention on phosphoinositide-specific phospholipase C may be determined by procedures described by Bennett et al, Molecular Pharmacology 32:587–593 (1987).

SPECIFIC EMBODIMENTS

The compounds of the present invention can be made by the synthetic chemical pathways which are illustrated here in general terms, and in the specific examples as well. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

The compounds of the invention (Formula 1) are prepared in accordance with the generalized steps outlined in Reaction Scheme 1. More specifically, with reference to Reaction Scheme 2, triethylsilyl-3-furaldehyde (Compound 5) is reacted with a trialkylsilyl cyanide, preferably with trimethylsilyl cyanide (Compound 4) in the presence of zinc bromide. This reaction is preferably conducted without a solvent, under a protective blanket of argon or other inert gas. The intermediate addition product (Compound 6) is preferably not isolated; rather it is reduced, preferably in the same reaction vessel, by addition of a hydride reducing reagent, such as lithium aluminum hydride. The product of the reaction, 4-(2-amino-1-hydroxy)ethyl-2-triethylsilylfuran (Compound 7) can be isolated after work-up by chromatography on a silica gel column. One starting material of the reaction, trielsilyl-3-furaldehyde (Compound 5) can be made in accordance with several procedures known in the chemical literature. The preferred method for the synthesis of Compound 5, however, is described in the application for U.S. Pat. Ser. No. 259,225, filed on Oct. 18, 1988, now allowed, and assigned to the same assignee as the present application. The process for the synthesis of this important starting material is also described here in detail in the ensuing section of specific Examples. The other starting material trimethylsilyl cyanide Compound 4 is available commercially, for example from Aldrich Chemical Company (Aldrich)).

Reaction Scheme 2

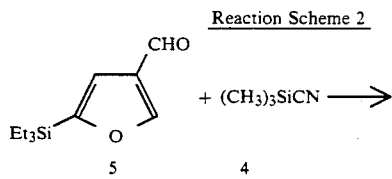

-continued
Reaction Scheme 2

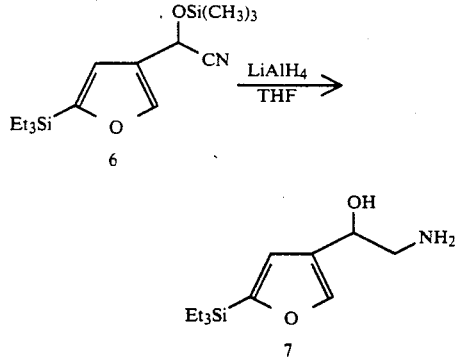

During the ensuing further description of general and specific procedures and examples it should be kept in mind, that although the description refers to the intermediate 4-(2-amino-1-hydroxy)ethyl-2-triethylsilylfuran (Compound 7), analogous trialxylsilyl compounds can also be used in these reactions.

Compounds of the invention which are carboxamides, sulfonamides or phoshonamides, (with reference to Formula 1, $Y=COR_4$, $Y=SO_2R_4$ or $Y=PO(OR_4)R_4$) can be made in accordance with Reaction Schemes 3, 4, and 5, in each of which, the intermediate 4-(2-amino-1-hydroxy)ethyl-2-triethylsilylfuran (Compound 7) is reacted with the appropriate carboxylic acid halide (scheme 3) sulfonic acid halide (Scheme 4) or phosphonic acid halide (Scheme 5) or with a like reagent conventionally used for the synthesis of a carboxamide. sulfonamide or phosphonamide from a corresponding amine. These reactions can be conducted in a variety of solvents; generally speaking tetrahydrofuran is highly suitable, and the presence of an acid acceptor, such as triethylamine is desirable. In Reaction Schemes 3, 4, and 5 $R_4$ is defined as in connection with Formula 1, and L represents a halogen (preferably chlorine) or other suitable leaving group. Acylation of the amine can also be conducted with a suitable acid anhydride, therefore $R_4$—L also represents an acid anhydride (L is a leaving group). Still other methods of introducing an acyl, sulfonyl or phosphonyl residue to the amino function of the molecule are possible. For example 4-(2-amino-1-hydroxy)ethyl-2-triethylsilylfuran (Compound 7) can be directly condensed with an acid $R_4COOH$ in the presence of dicyclohexylcarbodiimide and 4dimethylaminopyridine; in this case L represents OH.

REACTION SCHEME 3

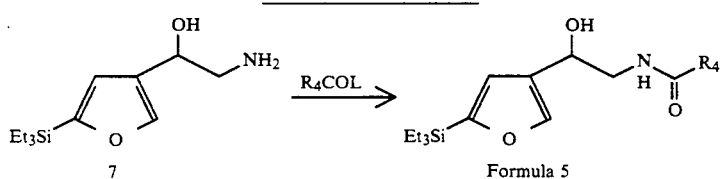

REACTION SCHEME 3
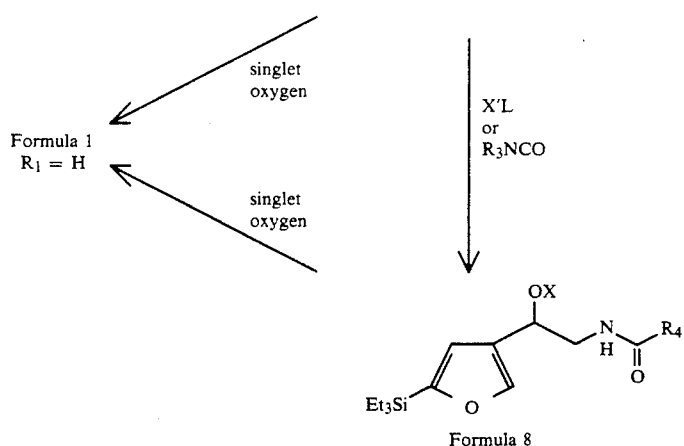
REACTION SCHEME 4
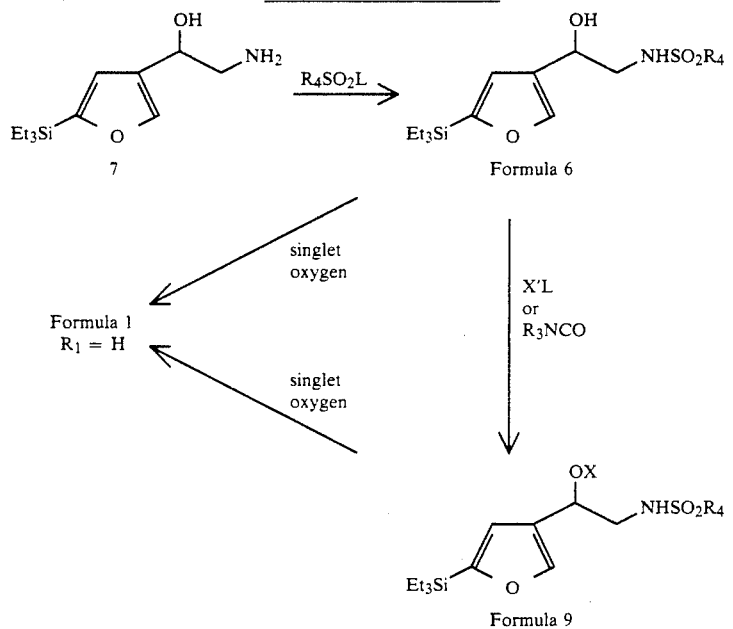
REACTION SCHEME 5
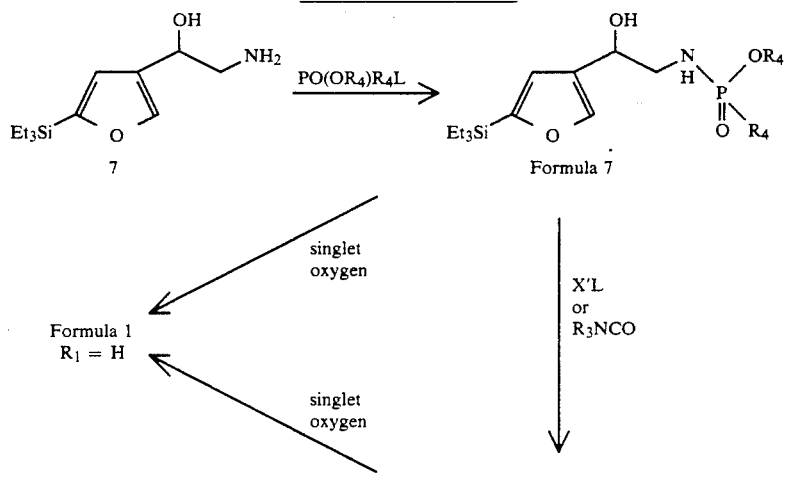

-continued

REACTION SCHEME 5

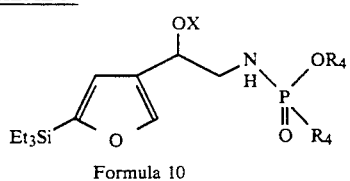

Formula 10

The intermediate 2-triethylsilylfuran carboxamides (Formula Scheme 3), 2-triethylsilylfuran sulfonamides (Formula 6 scheme 4) and 2-triethylsilylfuran phosphonamides (Formula 7 Scheme 5) can be further reacted, as is shown in the respective reaction Schemes to introduce a substituent into the alpha hydroxyl group in the side chain of the molecule. In other words, with reference to Formula 1, the X substituent is introduced into the molecule. This is shown in a generalized form on Reaction Schemes 3, 4 and 5, where the symbol X'—L means a suitable activated derivative which is capable of introducing the X substituent. L is a leaving group, usually halogen, and in most cases X' is the same radical as X. Typically, and by way of example, when the substituent on the alpha hydroxy group is acyl, then X'—L is an acid chloride; X'—L can also represent an acid anhydride. Similarly, when the substituent on the alpha hydroxy group is a sulfonic acid residue then X'—L typically is a sulfonyl chloride, and when the substituent on the alpha hydroxy group is a phosphonic acid residue then X'—L typically is a phosphonyl chloride, although other activated forms of sulfonic and phosphonic acids can also be used. Alternatively, to form an ester on the alpha hydroxy group, a condensation reaction with a suitable acid of the formula $R_3$—COOH can be conducted in the presence of dicyclohexylcarbodiimide and dimethylamino pyridine. In this latter situation L stands for OH.

Still referring to Reaction Schemes 3, 4, and 5, the alpha-hydroxyl group can also be reacted with a suitable chloroformate of the formula Cl-CO-OR$_3$ (R$_3$ is defined as in Formula 1 and in the Reaction Schemes 3, 4 and 5 X'=CO—OR$_3$ and L=Cl) so as to form a carbonate ester on the alpha hydroxy group. In order to form a carbamate derivative on the alpha hydroxy group, the intermediates of Formula 5, Formula 6 and of Formula 7, respectively, are reacted with an isocyanate derivative of the formula R$_3$—NCO (R$_3$ is defined as in Formula 1).

The 2-triethylsilylfuran intermediates bearing the X substituent are shown in the Reaction Schemes 3, 4 and 5 as Formula 8, Formula 9 and Formula 10, respectively.

Referring now to Reaction Scheme 6 and 7, synthetic schemes are disclosed for preparation of compounds of the invention where the nitrogen function in the side chain on the 4-position of the furan molecule has been converted to urea and carbamate derivatives, respectively. Thus, in accordance with Reaction Scheme 6, 4-(2-amino-1-hydroxy)ethyl-2-triethylsilylfuran (Compound 7) is reacted with an isocyanate derivative (R$_4$CNO, R$_4$ is defined as in connection with Formula 1), or with phosgene and an amine, preferably with a cyclic amine such as morpholine, methylsulfonamido morpholine, piperazine or substituted piperazine, to yield the intermediate 2-triethylsilylfuran urea derivatives of Formula 11. In Formula 11 R$_4$' is defined as R$_4$ in Formula 1, but also signifies the "residue" of cyclic amines, such as morpholine and piperazine.

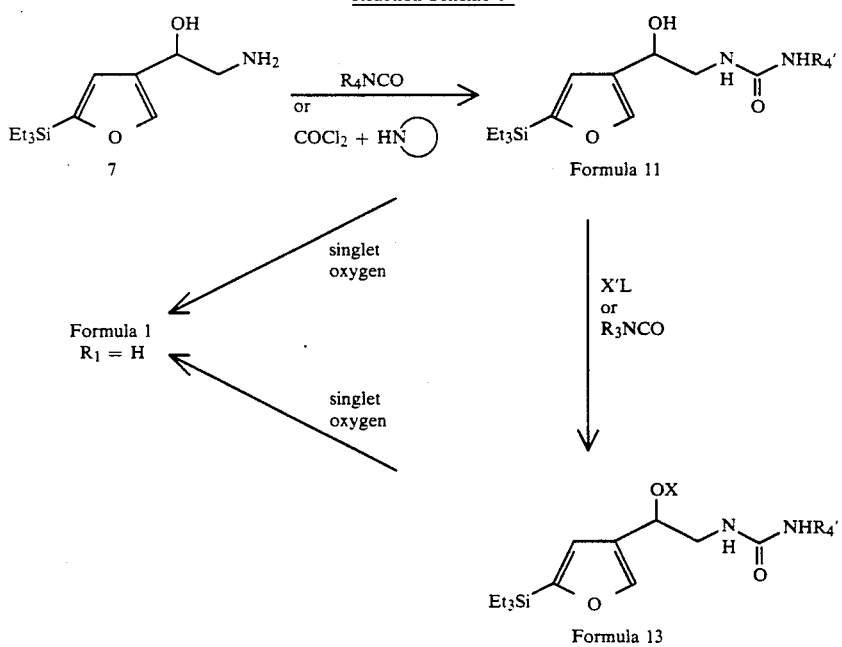

Reaction Scheme 6

Reaction Scheme 7

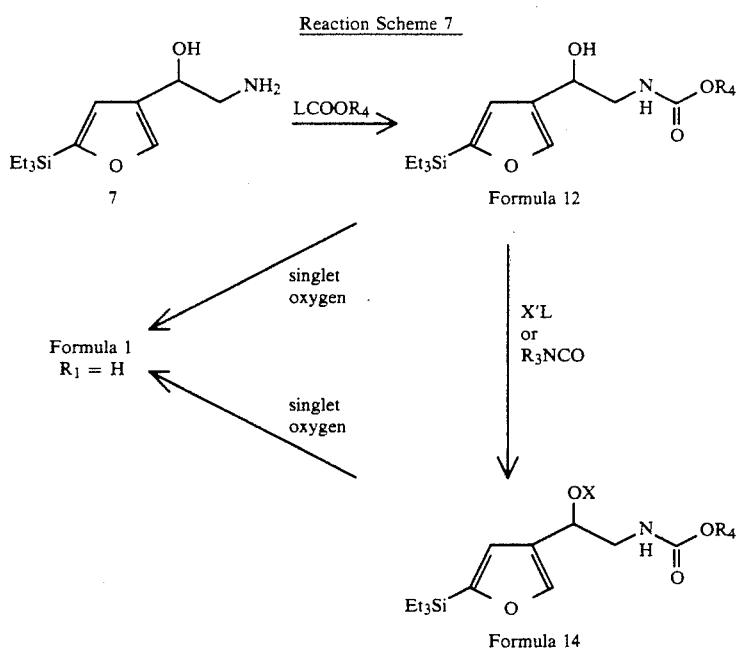

In accordance with Reaction scheme 7, the 2-triethylsilylfuran carbamate derivatives (Formula 12) can be obtained by reacting 4-(2-amino-1-hydroxy)ethyl-2-triethylsilylfuran (compound 7) with a suitable chloroformate L-COOR$_4$ (R$_4$ is defined as in Formula 1). The intermediates of Formula 11 and 12 in Reaction Scheme 6 and 7, respectively, can be further reacted, in the manner described above in connection with Reaction Schemes 3, 4 and 5, to introduce the X substituent on the alpha hydroxyl function in the side chain in the 4-position of the furan moiety. The intermediates bearing the X substituent are shown as Formula 13 and 14 in Reaction scheme 6 and 7, respectively.

In accordance with the presently described synthetic processes (which have been found to be best suited for making the novel compounds of the present invention) the intermediates of Formula 5 through 14, ar Ⓡconverted into the desired biologically active novel compounds in a reaction step which involves treating these intermediates with singlet oxygen. As a result of this reaction step, the trialkylsilyl (preferably triethylsilyl) group is "removed" from the furan molecule, an oxo function is introduced into the 2-position and a hydroxy function is introduced into the 5-position. This reaction is indicated on Reaction Schemes 3 through 7 to yield compounds of Formula 1 where R$_1$ is hydrogen. In the event, substitution on the 5-hydroxy group is desired, this can be accomplished with conventional means.

Referring back again to the reaction of the 2-triethylsilyl intermediates of Formula 5 through 14, with singlet oxygen, the conditions of these reactions are described below in connection with several specific examples. In general terms, the reaction of the intermediates of Formula 5 through 14, with singlet oxygen is preferably conducted in a mixture of water and acetone or in a mixture of water and tetrahydrofuran in the presence of an initiator, preferably Rose Bengal dye (preferably polymer bounded), which is added to the reaction mixture. The reaction mixture and vessel is flushed with oxygen and the reaction is conducted at low temperature, preferably at approximately 0° C., under a constant positive pressure of oxygen for a number of hours, typically 1 to 4 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

The following examples of specific compounds of the invention, and specific examples of the synthetic steps in which the compounds and certain intermediates are made, are set out to illustrate the invention, not to limit its scope.

SPECIFIC EXAMPLES

Example 1

5-Triethylsilyl-3-furaldehyde (Compound 5)

n-Butyl lithium (a 2.5M solution in hexane: 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethlsily-3-furaldehyde as a pale yellow oil, boiling point 85°-90°/0.4 torr.

IR (neat) 1680cm$^{-1}$.

$^1$H NMR (CDCl$_3$) 0.79 (q, 6H, J =7.3 Hz), 0.90 (t, 9H, J =7.3 Hz), 7.0 (s, 1H), 8.26 (s, 1H) and 9.95 (s, 1H).

$^{13}$C NMR (CDCL3) 2.9, 7.1, 117.2, 128.8, 155.6, 162.3 and 184.6.

HRMS m/e exact mass calculated for $C_{11}H_{18}O_2Si(M^+)$ 210.1076, found 210.1071.

4-(2-Amino-1-hydroxy)ethyl-2-triethylsilylfuran (Compound 7)

A mixture of 5-triethylsilyl-3-furaldehyde (Compound 5, 4.35g, 2.07 mmol), triethylsilyl cyanide (Compound 4, 3.0 ml, 22.7 mmol) and zinc bromide (ca. 10 mg) was stirred under argon at room temperature for 19 hours. After cooled to 0°, lithium aluminum hydride (a 1.0M solution in tetrahydrofuran; 31.0 ml, 31.0 mmol) was added dropwise. Stirring was continued for 3 hours while the cooling bath was warmed to room temperature. The mixture was recooled to 0° and was quenched with dilute sodium hydroxide. After the aluminum salt was coagulated by the addition of sodium sulfate, the mixture was filtered. Evaporation of the filtrate gave a residue which was purified by a silica column using 20% methanol/chloroform/0.2% triethylamine to give the title amino alcohol as a pale yellow solid.
$^1$HNMR(CDCl$_3$) 0.73 (q, 6H, J =8.2 Hz), 0.97 (t, 9H, J =8.2 Hz), 2.05 (br, 3H), 2.87 (dd, 1H, J =7.6 Hz, 12.7 Hz), 3.00 (dd, 1H J =12.7 Hz, 4.0Hz), 4.62 (dd, 1H, J =4.0 Hz, 7.4Hz), 6.61 (s, 1H) and 7.61 (s, 1H).

4-(2-Undecanylamido-1-hydroxy)ethyl-2-triethylsilylfuran (Compound 8) and 4-(2-undecanylamido-1-dodecanoyloxy)ethyl-2-triethylsilylfuran (Compound 9)

Dodecanoyl dichloride (0.41 ml, 1.76 mmol) was added dropwise to a solution of 4-(2-amino-1-hydroxy)ethyl-2-triethylsilylfuran (Compound 7) (404.7 mg, 1.6B mmol) and triethylamine (0.25 ml, 1.76 mmol) in tetrahydrofuran (4 ml) at 0°. Stirring was continued for 14 hours while the cooling bath attained room temperature. The mixture was evaporated to give a residue which was purified by a silica column using 20% ethyl acetate/hexane. Fractions with R$_f$ of about 0.19 (20% ethyl acetate/hexane) on evaporation gave 4-(2-undecanylamido-1-dodecanoyloxy)ethyl-2-triethylsilylfuran (compound 9). Further elution of the column with 40% ethyl acetate/hexane gave 4-(2-undecanylamido-1-hydroxy)ethyl-2-triethylsilylfuran (Compound 8 R$_f$ 0.19; 40% ethylacetate/hexane).

4-(2-Undecanylamido-1-dodecanoyloxy)ethyl-2-triethylsilylfuran (Compound 9)

$^1$HNMR(CDCl$_3$): 0.75 (q, 6H, J =7.9 Hz), 0.88 (t, 6H, J =6.9Hz), 0.97 (q, 9H, J =7.4 Hz),1.25 (br s 32H), 1.60 (m, 4H), 2.15 (t, 2H J =8.0 Hz), 2.33 (t, 2H J =7.6 Hz), 3.68 (m, 2H), 5.65 (br t, 1H), 5.90 (br t, 1H), 6.58 (s, 1H) and 7.63 (s, 1H). MS (m/e % abundance) 606[(M+H)$^+$, 1], 450(2), 424(4), 423(10), 408(10), 407(32), 406(100), 405(5), 224(8), 200(2) 183(2) and 104(2).

4-(2-Undecanylamido-1-hydroxy)ethyl-2-triethylsilylfuran (Compound 8)

$^1$HNMR (CDCl$_3$) 0.75 (q, 6H, J =7.9 Hz), 0.89 (t, 3H, J=7.1 Hz), 0.98 (q, 9H, J =7.1 Hz), 1.27 (br s, 16H), 1.65 (m, 2H), 2.21 (t, 2H, J =7.3 Hz), 3.08 (d, 1H, J =3.8 Hz), 3.38 (2dd, 1H, J =15.0 Hz, 7.5 Hz and 6.0 Hz), 3.70 (2dd, 1H, J =15.0 Hz, 7.5 Hz and 3.0 Hz), 4.85 (m, 1H), 5.95 (br t, 1H), 6.62 (s, 1H). HRMS exact mass calculated for $C_{24}H_{45}SiNO_3(M^+)$ 423.3169, found 423.3166.

4-(2-Undecanylamido-1-hydroxy)ethyl-5-hydroxy-2(5H)-furanone (Compound 10)

A mixture of 4-(2-undecanylamido-1-hydroxy)ethyl-2-triethylsilylfuran (Compound s, 300 mg, 0.71 mmol), water (a few drops) and Rose Bengal (5 mg) in acetone (7 ml) was exposed to singlet oxygen at 0° for 1 hour. The residue, after solvent removal, was purified on preparative silica plates (developed with 5% methanol/dichloromethane) to give the title furanone.
$^1$HNMR(CD30D): 0.90 (br t, 3H), 1.29 (br s, 16H), 1.55 (m, 2H), 2.19 (t, 2H, J =7.3 Hz), 3.50 (br m, 2H), 4 60 (br, 1H), 6.06 (s, 1H) and 6.15 (br s, 1H).
$^{13}$CNMR(CD$_3$OD): 14.5, 23.7, 23.9, 27.0, 27.1, 29.8, 29.9, 30.0, 30.2, 30.4, 30.6, 30.7, 31.1, 31.3, 33.0, 33.2, 36.9, 44.4, 44.5, 44.6, 68.2, 100.3, 100.4, 119.6, 171.2, 172.6 and 176.9. HRMS exact mass calculated for $C_{18}H_{31}NO_5$ (M$^+$) 342.2280 found 342.2293.

Example 2

4-(1-Acetoxy-2-undecanylamido)ethyl-2-triethylsilylfuran (Compound 11)

A mixture of 4-(2-undecanylamido-1-hydroxy)ethyl-2-triethylsilylfuran (Compound 8, 244.3 mg, 0.58 mmol), acetic anhydride (0.5 ml) and pyridine (0.5 ml) was stirred at room temperature for 16 hours. After most of the solvent was removed, the residue was purified by preparative silica TLC using 60% ethyl ether/hexane to give the title ester as a colorless solid.
$^1$HNMR(CDCl$_3$) 0.77 (q, 6H, J =7.5 Hz), 0.91 (t, 3H, J =6.8 Hz), 1.00 (t, 9H, J =7.3 Hz), 1.29 (br s, 16H), 1.60 (m, 2H), 2.13 (s 3H) 2.19 (t 2H J 7 9 Hz) 3.70 (m 2H) 5.70 (br t, 1H), 6.95 (m, 1H), 6.63 (s, 1H) and 7.67 (s, 1H). HRMS exact mass calculated for $C_{26}H_{47}NO_4Si(M^+)$ 465.3274, found 465.3283.

4-(1-Acetoxy-2-undecanylamido)ethyl-5-hydroxy-2(5H)-furanone (Compound 12)

A mixture of 4-(1-acetoxy-2-undecanylamido)ethyl-2-triethylsilylfuran (Compound 11, 160 mg, 0.34 mmol), Water (a few drops) and Rose Bengal (3 mg) in acetone (7 ml) was exposed to singlet oxygen at 0° for 2 hours. The residue, after solvent removal, was purified by preparative silica plates (developed with 40% ethyl acetate/hexane) to give the title furanone.
$^1$HNMR(CDCl$_3$): 0.89 (t, 3H, J =6.8 Hz), 1.27 (br s, 16H), 1.65 (m, 2H), 2.18 (s, 3H), 2.20 (m, 2H), 3.35 (br m, 1H), 4.25 (br m, 1H), 5.60 (brs, 1H), 5.95 (br s, 1H), 6.10 (m, 1H), 6.20 (m, 1H) and 7.20 (br m, 1H).
$^{13}$CNMR(CDCl$_3$): 14.0, 20.7, 22.6, 25.6, 25.7, 28.8, 28.9, 29.1, 29.2, 29.4, 29.5, 29.8, 31.8 36.2, 40.9, 41.0, 41.1, 50.5, 69.3, 69.4, 69.5, 98.7, 120.2, 120.3, 120.4, 169.5, 169.7, 175.9, 176.0 and 176.1
HRMS exact mass calculated from $C_{20}H_{34}NO_6(M^+)$ 384.2386, found 384.2381.

Example 3

4-(2-Undecanylamido-1-dodecanoyloxy)ethyl-5-hydroxy-2(5H)-furanone (Compound 13)

A mixture of 4-(2-undecanylamido-1-dodecanoyl-)ethyl-2-triethylsilylfuran (Compound 9, 145 mg, 0.24 mmol), Rose Bengal (ca. 5 mg) and a few drops of water in tetrahydrofuran (7 ml) was exposed to singlet oxygen at 0° for 1 hour. The residue, after solvent removal, was purified by preparative silica TLC plates using 40% ethyl acetate/hexane to give the title furanone as a pale yellow oil.

¹HNMR(CDCl₃): 0.93 (t, 6H, J = 7.0 Hz), 1.31 (br, s, 32H), 1.60 (m, 4H), 2.25 (m, 2H), 2.40 (t, 2H, J = 7.6 Hz), 3.35 (2 br t, 1H), 4.30 (m, 1H), 5.64 (br s, 1H), 5.96 (s, 1H), 6.05–6.20 (m, 3H) and 7.65 (br m 1H). MS (m/e, % abundance): 523(M+, 15), 522 (13), 521 (24), 339 (12), 326 (12), 324 (16), 310 (25), 309 (21), 308 (100), 307 (19), 306 (28), 264 (18), 218 (23), 201 (71), 200 (64), 183 (60), 181 (43), 126 (81) 125 (67), 98 (43) and 83 (39).

Example 4

4-[(1-Hydroxy-2-dodecanesulfonylamido)ethyl]-2-triethylsilylfuran (Compound 14)

A mixture of 4-(2-amino-1-hydroxy)ethyl-2-triethylsilylfuran (Compound 7, 694.2 mg, 2.88 mmol), dodecanesulfonyl chloride (930 mg, 3.45 mmol) and triethylamine (0.48 ml, 3.45 mmol) in tetrahydrofuran (10 ml) was stirred at room temperature for 2 days. The mixture was quenched with water and was extracted with ethyl ether. Evaporation of the dried (magnesium sulfate) extracts gave an oil, which was purified by a silica column using 55% ethyl ether/hexane to give the title compound.

¹HNMR(CDCl₃): 0.76 (q, 6H, J = 8.0 Hz), 0.88 (t, 3H, J = 6.9 Hz), 0.98 (t, 9H, J = 8.0 Hz), 26 (m 16H) 1.38 (m 2H) 1.81 (m 2H) 2.21 (m, 1H), 3.0 (m, 2H), 3.35 (m, 2H), 4.62 (m, 1H), 4.85 (m 1H), 6.61 (s, 1H) and 7.65 (s, 1H).
¹³CNMR(CDCl₃): 3.0, 7.1, 13.9, 22.5, 23.4, 28.2, 29.0, 29.1, 29.2, 29.4, 29.5, 31.8 49.3, 52.6, 66.4, 119.0, 125.3, 143.7 and 159.4. HRMS exact mass calculated for $C_{24}H_{47}NO_4SSi$:(M+) 473.2995 found 473.3004.

4-[(1-Hydroxy-2-dodecanesulfonylamide)ethyl]-5-hydroxy-2(5H)-furanone (Compound 15)

A mixture of 4-[(1-hydroxy-2-dodecanesulfonylamido)ethyl-]-2-triethylsilylfuran (Compound 14, 200 mg, 0.42 mmol), water (a few drops) and Rose Bengal (5 mg) in acetone (10 ml) was exposed to singlet oxygen at 0° for 2 hours. The residue, after solvent removal, was purified by preparative silica plates (developed with 20% methanol dichloromethane) to give the titled furanone. ¹HNMR (CDCl₃): 0.88 (t, 3H, J = 6.9 Hz), 1.26 (m, 18H), 1.75 (m, 2H), 3.05 (m, 2H), 3.30 (m, 1H), 3.42 (m, 1H), 4.69 (br, 1H), 6.20 (br, 1H) and 6.29 (br, 1H).
¹³CNMR(CDCl₃): 13.9, 22.5, 23.3, 28.2, 29.1, 29.2, 29.3, 29.5, 31.7, 46.3, 46.4, 52.6, 67.3, 67.4, 98.3, 98.4, 119.9, 167.0, 168.0, 172.2 and 172.3. HRMS exact mass calculated for $C_{18}H_{35}N_2O_5S[(M+NH_4)-H_2O]$ 391.2267, found 391.2249.

Example 5

4-[1-Acetoxy-2-(dodecanesulfonylamido)ethyl]-2-triethylsilylfuran (Compound 16)

A mixture of 4-[1-hydroxy-2-(dodecansulfonylamido)ethyl]-2-triethylsilylfuran (Compound 14, 228 mg, 0.48 mmol), acetic anhydride (55 ul, 0.58 mmol) and pyridine (47 ul, 0.58 mmol) in dichloromethane (5 ml) was stirred at room temperature for 14 hours. After most of the solvent was removed, the residue was redissolved in ether and washed with aqueous copper sulfate and water. Evaporation of the dried (magnesium sulfate) organic phase gave an oil, which was purified by a silica column using 45% ethyl ether/hexane to give the titled ester.

¹HNMR(CDCl₃): 0.76 (q, 6H, J = 7.4 Hz), 0.88 (t, 3H, J = 5.9 Hz), 0.97 (t, 9H, J = 7.4 Hz), 1.25 (m, 18H), 1.76 (m, 2H), 2.10 (s, 3H), 2.97 (m, 2H), 3.50 (t, 2H, J = 5.9 Hz), 4.30 (m, 1H), 5.87 (t, 1H, J = 5.9 Hz), 6.59 (s, 1H) and 7.66 (s, 1H).

4-[1-Acetoxy-2-idodecanesulfonylamido)ethyl]-5-hydroxy-2(5H)-furanone (Compound 17)

A mixture of 4-[1-acetoxy-2-dodecanesulfonylamido)ethyl]-2-triethylsilylfuran (Compound 16, 196 mg, 0.38 mmol), water (2 drops) and Rose Bengal (5 mg) in acetone (15 ml) was exposed to singlet oxygen at 0o for 2 hours. The residue, after solvent removal, was purified by preparative silica plates (developed with 10% methanol/chloroform) to give the title furanone.
¹HNMR(CDCl₃) 0.88 (t, 3H, J = 6.4 Hz), 1.25 (m, 18H), 1.75 (m, 2H), 2.17 (s, 3H), 3.0 (m, 2H), 3.57 (br s, 2H), 5.60 (m, 1H), 6.16 (s, 1H) and 6.18 (s, 1H).
¹³CNMR(CDCl₃): 14.1, 18.2, 20.7, 22.6, 23.5, 28.2, 29.0, 29.1, 29.3, 29.5, 29.6, 29.8, 44.4, 53.4, 58.4, 69.1, 98.1 121.2, 162.7, 169.9 and 170.1. LRMS (m/e, % abundance) 391 (M+, 28), 390(15), 389(37), 376(23), 375(100), 374(12), 358(38), 356(18), 328(23), 327(12), 312(14), 268(14), 267(84), 252(49), 208(28), 207(11), 201(15) and 185(15).

Example 6

4-[1-Hydroxy-2-(3-carboxypropaneamido)1ethyl-2-triethylsilylfuran (Compound 18)

A mixture of 4-(2-amino-1-hydroxy)ethyl-2-triethylsilylfuran (Compound 7, 300 mg, 1.24 mmol) and glutaric anhydride (212 mg, 1.86 mmol) in dichloromethane (5 ml) was stirred at room temperature for 2 days. The mixture was acidified with dilute hydrochloric acid and was extracted thoroughly with ethyl acetate. Evaporation of the dried (magnesium sulfate) extracts gave an oil, which was purified by preparative silica plates (developed with 20% methanol/chloroform) to give the title furan.

¹HNMR(CDCl₃) 0.74 (q, 6H, J = 8.0 Hz), 0.95 (t, 9H, J = 8.0 Hz), 1.94 (m, 2H), 2.29 (t, 2H, J = 7.2 Hz), 2.38 (t, 2H, J = 7.8 Hz), 3.30 (m, 1H), 3.68 (m, 1H), 4.80 (dd, 1H, J = 3.1 Hz, 8.5 Hz), 5.60 (br, 1H), 6.59 (br s, 2H) and 7.58 (s, 1H).
¹³CNMR(CDCl₃): 3.1, 7.2, 20.8, 33.0, 35.1, 46.1, 66.1, 119.1, 125.7, 143.5, 159.5, 174.3 and 176.9. LMRS (m/e % abundance) 356[(M+H),+8), 339(24), 338(100), 320(13), 308(22), 224(29), 145(53), 127(23), 115(12) and 87(11).

4-[1-Dodecanoyloxy-2-(3-carboxypropeneamido)]1ethyl-2-triethylsilylfuran (Compound 19)

A mixture of 4-[1-hydroxy-1-(3-carboxypropaneamido)]ethyl-2-triethylsilylfuran (Compound 18, 137.5 mg, 0.3 mmol), dodecanoyl chloride (0.22 ml, 0.92 mmol) and triethylamine (0.36 ml, 2.58 mmol) in dichloromethane (5 ml) was stirred at room temperature for 14 hours. The mixture was quenched with dilute hydrochloric acid and was extracted with ethyl acetate. Evaporation of the dried (magnesium sulfate) extracts gave an oil, which was purified by a silica column using 10% methanol/chloroform to give the title furan.

¹H NMR (CDCl₃) 0.73 (q, 6H, J = 8.0 Hz), 0.88 (t, 3H, J = 6.4 Hz), 0.97 (t, 9H, J = 8.0 Hz), 1.75 (m, 14H), 1.60 (m, 2H), 1.95 (p, 2H, J = 7.2 Hz), 2.26 (t, 2H, J = 7.2 Hz), 2.33 (t, 2H, J = 7.6 Hz), 2.40 (t, 2H, J = 7.2 Hz), 3.76 (m, 2H), 5.85 (br, 1H), 5.90 (dd, 1H, J = 7.9 Hz, 4.3 Hz), 6.58 (s, 1H) and 7.63 (s, 1H).

$^{13}$CNMR(CDCl$_3$): 3.1, 7.2, 20.6, 22.6, 24.9, 29.1, 29.2, 29.3, 29.4, 29.6, 29.8, 31.9, 32.9, 34.4, 35.2, 43.4, 67.4, 119.3, 122.0, 144.6, 159.9, 172.5, 173.6 and 177.6. LRMS (m/e, % abundance) 538[(M+H)$^+$, (1)], 453(2), 452(5), 406(28), 340(25), 339(52), 338(100), 337(6), 320(27) and 308(8).

Example 7

4-[(1-Hydroxy-2-(10-carboxydecaneamido)1ethyl-2-triethylsilylfuran (Compound 20)

A mixture of 4-(2-amino-1-hydroxy)ethyl-2-triethylsilylfuran (Compound 7, 208.0 mg, 0.86 mmol), dodecanedioic acid (199.0 mg, 0.86 mmol), dicyclohexylcarbodiimide (178 mg, 0.86 mmol) and 4-dimethylaminopyridine (105 mg, 0.86 mmol) in dichloromethane (5 ml) was stirred at room temperature for 16 hours. The mixture was quenched with dilute hydrochloric acid and was extracted with ethyl acetate. Evaporation of the dried (magnesium sulfate) extracts gave a residue, which was purified by a silica column using 5% methanol/chloroform to give the title furan.

$^1$HNMR(CDCL$_3$): 0.76 (q, 6H, J =8.0 Hz), 0.97 (t, 9H, J =8.0 Hz), 1.29 (br s, 12H), 2.21 (t, 2H, J =7.9 Hz), 2.35 (t, 2H, J =7.2 Hz), 3.35 (m, 1H), 3.60 (m, 1H), 4.83 (dd, 1H, J =7.8 Hz, 3.0 Hz), 6.10 (t, 1H, J =2.9 Hz), 6.61 (s, 1H) and 7.62 (s, 1H).

$^{13}$CNMR(CDCl$_3$) 3.1, 7.2, 24.6, 24.7, 24.8, 25.6, 28.8, 28.9, 29.0, 29.1, 33.6, 34.0, 36.5, 46.2, 66.5, 119.1, 126.0, 143.5, 159.6, 174.8 and 178.4. HRMS exact mass Calculated for C$_{24}$H$_{43}$SiNO$_5$(M+) 453.2911, found 453,2913.

4-[1-Dodecanoyloxy-2-(3-carboxypropaneamido)1ethyl-5-hydroxy-2(5H)-furanone (Compound 21a)

A mixture of 4-[1-dodecaneyloxy-2-(3-carboxypropaneamido)]ethyl-2-triethylsilyl furan (Compound 19, 39.5 mg, 0.07 mmol), water (a few drops) and Rose Bengal (5 mg) was exposed to singlet oxygen at 0o for 2 hours. The residue, after solvent removal, was purified by preparative silica plates (developed with 10% methanol/chloroform containing 0.5% acetic acid) to give the title furanone.

$^1$HNMR(CD$_3$OD): 0.79 (t, 3H, J=6.2 Hz), 1.18 (m, 16H), 1.56 (t, 2H, J =7.3 Hz), 1.76 (p, 2H, J =7.5 Hz), 2.13 (t, 2H, J =7.5 Hz), 2.19 (t, 2H, J =7.5 Hz), 2.55 (t, 1H, J =7.5 Hz), 3.50 (br m, 2H), 5.64 (br, 1H), 5.99 (br, 1H) and 6.11 (br, 1H). $^{13}$CNMR(CD30D): 14.4, 22.3, 23.7, 25.8, 30.2, 30.4, 30.5, 30.6, 30.8, 33.1, 34.1, 34.8, 35.9, 41.9, 70.0, 100.0, 120.4, 166.3, 171.9, 174.0 and 176.0.

4-[(1-Hydroxy-2-(10-carboxydecaneamido)1ethyl-5-hydroxy-2(5H)-furanone (Compound 21)

A mixture of 4-[(1-hydroxy-2-(10-carboxydecaneamido)]ethyl-2-triethylsilylfuran (Compound 20, 15 mg, 0.19 mmol), water (a few drops) and Rose Bengal (5 mg) in acetone (7 ml) was exposed to singlet oxygen at 0° for 2 hours. The residue, after solvent removal, was purified by a silica column using 10% methanol/chloroform to give the title furanone.

$^1$H NMR (CDCl$_3$) 1.29 (m, 12H), 1.60 (m, 4H), 2.18 (t, 2H, J =7.0 Hz), 2.27 (t, 2H, J =7.4 Hz), 3.40 (m 1H), 3.55 (m, 2H), 6.03 (br, 1H), and 6.19 (br, 1H). $^{13}$CNMR(CDCl$_3$): 26.0, 27.0, 30.1, 30.2, 30.3, 30.4, 30.5, 34.9, 36.9, 44.4, 49.7, 68.4, 99.7, 119.4, 172.0, 172.6, 176.9 and 177.7. LRMS (m/e, % abundance) 371 (M+32), 355(17), 358(38), 249(14), 248(100), 230(41) and 229(11).

Example 8

4-[(1-Acetoxy-2-(10-carboxydecaneamido)1ethyl-2--triethylsilylfuran (Compound 22)

A mixture of 4-[(1-hydroxy-2-(10-carboxydecaneamido)]ethyl-2-triethylsilylfuran (Compound 20, 53.4 mg, 0.12 mmol), triethylamine (60 ul, 0.45 mmol) and acetic anhydride (42 ul, 0.45 mmol) in dichloromethane (5 ml) stirred at room temperature for 14 hours. The mixture was quenched with dilute hydrochloric acid and was extracted with ethyl acetate. Evaporation of the dried (magnesium sulfate) extracts gave an oil, which was purified by a silica column using 5% methanol/chloroform to give the title furanone.

$^1$HNMR(CDCl$_3$): 0.76 (q, 6H, J =8.0 Hz), 0.97 (t, 9H, J =8.0 Hz), 1.27 (m, 16H), 1.63 (m, 4H), 2.09 (s, 3H), 2.16 (t, 2H, J =8.0 Hz), 2.34 (t, 2H, J =7.4 Hz), 3.67 (m, 2H), 5.76 (br t, 1H), 5.90 (dd, 1H, J =7.2 Hz, 5.0 Hz), 6.59 (s, 1H) and 7.64 (s, 1H).

$^{13}$CNMR(CDCl$_3$) 2.9, 7.0, 20.9, 24.5, 24.7, 25.3, 25.4, 28.6, 28.7, 28.9, 33.4, 33.8, 36.5, 43.1, 67.7, 119.5, 122.1, 144.9, 160.3, 171.0, 173.8 and 178.9. HRMS exact mass calculated for C$_{26}$H$_{45}$NO$_6$Si(M+) 495.3016, found 495.2997.

4-[(1-Acetoxy-2-(10-carboxydecaneamido)1ethyl-5-hydroxy-2(5H)-furanone (Compound 23)

A mixture of 4-[(1-acetoxy-2-(10-carboxydecaneamido)]ethyl-2-triethylsilylfuran (Compound 22, 53.6 mg, 0.12 mmol), water (a few drops) and Rose Bengal (3 mg) in acetone (7 ml) was exposed to singlet oxygen at 0° for 2 hours. The residue, after solvent removal, was purified by preparative silica plates (developed with 10% methanol/chloroform) to give the title furanone.

$^1$HNMR(CDCl$_3$) 1.26 (m, 12H), 2.55 (m, 4H), 2.15 (m, 5H), 2.35 (t, 2H, J =7.3 Hz), 3.35 (m, 1H), 3.45 (br, 1H), 3.90 (br, 1H), 4.20 (m, 1H), 5.59 (br, 1H), 5.65 (br, 1H), 5.97 (br, 1H), 6.00 (br, 1H) 6.10 (br, 1H), 6.15 (br, 1H), 6.30 (br, 1H) and 6.40 (br, 1H). $^{13}$CNMR(CDCl$_3$) 20.8, 24.6, 25.5, 28.9, 29.0, 29.1, 29.3, 33.8, 36.3, 41.4, 69.8, 98.6, 120.4, 163.1, 169.1, 169.2, 176.0 and 178.8. LRMS (m/e % abundance) 395[(M+-H$_2$O), 0.4], 369(7), 355(10), 354(14), 353(40), 336(12), 249(14), 248(100) and 230(29).

Example 9

N-(Methanesulfonyl)piperazine (Compound 24)

A mixture of methanesulfonyl chloride (1.85 ml, 24 mmol) and piperazine (2.06 g, 24 mmol) in dichloromethane (60 ml) was stirred at room temperature for 14 hours. The mixture was basified with aqueous sodium hydroxide and filtered. The filtrate was washed with water, dried (magnesium sulfate) and evaporated down to give the title sulfonamide.

$^1$HNMR(CDCl$_3$): 1.75 (br s, 1H), 2.78 (s, 3H), 2.97 (t, 4H, J=5.1 Hz) and 3.19 (t, 4H, J=7.5 Hz). LRMS (m/e, % abundance) 165[(M+H)$^+$, 7), 164M$^{30}$, 5), 85(100) and 56(68).

4-[1-Hydroxy-2-(N'-methanesulfonylpiperazine)amido1ethyl-2-triethylsilylfuran (Compound 25) and
4-[1-hydroxy-2-(N',N'-diethyl)amido]ethyl-2-triethylsilylfuran (Compound 26)

Phosgene (a 20% solution in toluene; 0.46 ml, 0.90 mmol) was added dropwise to a mixture of N-(methanesulfonyl)piperazine (Compound 24, 147.4 mg, 0.90 mmol) and triethylamine (0.13 ml, 0.90 mmol) in dichloromethane (3 ml) at room temperature. After 1 hour, 4-(2-amino-1-hydroxy)ethyl-2-triethylsilylfuran (Compound 7, 217 mg, 0.90 mmol) was added. Stirring was continued at room temperature for 14 hours. The mixture was quenched with water and was extracted with ethyl acetate. Evaporation of the dried (magnesium sulfate) extracts gave a residue, which was purified by a silica column using 80% ethyl acetate/hexane to give 4-[1-hydroxy-2-(N',N'-diethyl)amido]-ethyl-2-triethylsilylfuran (Compound 26, $R_f$ 0.27, 80% ethylacetate/hexane). Subsequent elution with ethyl acetate gave 4-[1-hydroxy-2-(N'-methanesulfonylpiperazine)amido]-ethyl-2-triethylsilylfuran (Compound 25, $R_f$ 0.21; ethyl acetate/hexane).

4-[1-Hydroxy-2-(N'-methanesulfonylpiperazine)amido]ethyl-2-triethylsilylfuran (Compound 25), $^1$HNMR(CDCl$_3$): 0.79 (q, 6H, J =8.0 Hz), 1.00 (t, 9H, J =8.1 Hz), 1.70 (br, 1H), 2.83 (s, 3H), 3.26 (t, 4H, J =4.8 Hz), 3.40 (m, 1H), 3.55 (t, 4H, J =4.8 Hz), 3.60 (m, 1H), 4.84 (dd, 1H, J =7.9 Hz, 3.2 Hz), 5.03 (br, 1H), 6.64 (s, 1H) and 7.65 (s, 1H). HRMS exact mass calculated for C$_{18}$H$_{33}$N$_2$O$_5$SSi(M+) 431.1910, found 431.1895.

4-[1-Hydroxy-2-(N',N'-diethyl)amido]ethyl-2-triethylsilylfuran (Compound 26)

$^1$HNMR(CDCl$_3$): 0.73 (q, 6H, J =7.5 Hz), 1.00 (t, 9H, J=, J =7.4 Hz), 1.16 (t, 6H, J =7.1 Hz), 3.30 (q, 4H, J =7.1 Hz), 3.40 (m, 1H), 3.65 (m, 1H), 4.33 (d, 1H, J =4.1 Hz), 4.80 (br t+m, 2H), 6.65 (s, 1H) and 7.64 (s, 1H). HRMS exact mass calculated for C$_{17}$H$_{32}$N$_2$O$_3$Si(M+) 340.2182, found 340.2171.

4-[1-Dodecaneyloxy-2-(N'-methanesulfonylpiperazine)amido1ethyl-2-triethylsilylfuran (Compound 27)

A mixture of 4-[1-hydroxy-2-(N'-methanesulfonylpiperazine)amido] -ethyl-2-triethylsilylfuran (Compound 26, 100 mg, 0.23 mmol), dodecanoyl chloride (95 ul, 0.41 mmol) and triethylamine (40 ul, 0.28 mmol) in dichloromethane (7 ml) was stirred at room temperature for 14 hours. The mixture was quenched with water and was extracted with ethyl acetate. Evaporation of the dried (magnesium sulfate) extracts gave an oil, which was purified by preparative silica plates (developed with 45% ethylacetate/hexane) to give the title furan.

$^1$HNMR(CDCl$_3$): 0.76 (q, 6H, J =8.0 Hz), 0.88 (t, 3H, J =6.0 Hz), 0.97 (t, 9H, J =8.0 Hz), 1.25 (m, 14H), 2.34 (t, 2H, J =7.6 Hz), 2.79 (s, 3H), 3.21 (t, 4H, J =4.9 Hz), 3.46 (m, 4H), 3.65 (m, 2H), 4.92 (br t, 1H), 5.94 (dd, 1H, J =8.0 Hz, 4.0 Hz), 6.59 (s, 1H) and 7.64 (s, 1H).

$^{13}$CNMR(CDCl$_3$): 3.1, 7.2, 14.0, 22.6, 24.9, 29.0, 29.2, 29.4, 29.5, 31.8, 34.5, 43.6, 45.4, 45.5, 68.1, 119.3, 122.1, 144.4, 156.8, 159.9 and 173.9. HRMS exact mass calculated for C$_{30}$H$_{55}$N$_3$O$_6$SSi(M+) 413.3581, found 413.3562.

4-[1-Dodecaneyloxy-2-(N'-methanesulfonylpiperazine)amidolethyl-5-hydroxy-2(5H)-furanone (Compound 28)

A mixture of 4-[1-dodecanoyloxy-2-(N'methanesulfonylpiperazine)amido]ethyl-2-triethylsilylfuran (Compound 27, 61 mg, 0.11 mmol), water (a few drops) and Rose Bengal (3 mg) in acetone (7 ml) was exposed to singlet oxygen at 0° for 2 hours. The residue, after solvent removal, was purified by a silica column using 7.5% methanol/chloroform to give the title furanone.

$^1$HNMR(CDCl$_3$): 0.88 (t, 3H, J =6.9 Hz), 1.26 (m, 16H), 1.61 (m, 2H), 2.40 (t, 2H, J =6.9 Hz), 2.80 (s, 3H), 3.19 (t, 4H, J =5.0 Hz), 3.50 (m, 5H), 4.18(m, 1H), 5.05 (m, 1H), 5.56 (br d, 1H, J =1.3 Hz), 5.90 (br, 1H), 6.12 (br, 1H) and 7.65 (m, 1H).

$^{13}$CNMR(CDCl$_3$): 14.5, 23.0, 25.1, 29.5, 29.6, 29.7 29.8, 30.0, 32.2, 34.4, 35.1, 43.1, 44.1, 45.7, 70.1, 99.3, 120.6, 158.0, 169.8, 169.9 and 172.6. HRMS exact mass calculated for C$_{24}$H$_{40}$N$_3$O$_7$S (M+-OH) 514.2587, found 514.2591.

Example 10

4-[1-Dodecaneyloxy-2-(N',N'-diethyl)amido1ethyl-2-triethylsilylfuran (Compound 29)

A mixture of 4-[1-hydroxy-2-(N',N'-diethyl)amido]ethyl-2-triethylsilylfuran (Compound 26, 80 mg, 0.24 mmol), dodecanoyl chloride 65 ul, 0.28 mmol) and triethylamine (40 ul, 0.28 mmol) in dichloromethane (7 ml) was stirred at room temperature for 14 hours. The mixture was quenched with water and was extracted thoroughly with ethyl acetate. Evaporation of the dried magnesium sulfate) extracts gave an oil, which was purified by preparative silica plates (developed with 60% ethyl ether/hexane) to give the title furan.

$^1$HNMR(CDCl$_3$): 0.75 (q, 6H, J =8.0 Hz), 0.88 (t, 3H, J =7.0 Hz), 0.96 (t, 9H, J =8.0 Hz), 1.10 (t, 6H, J =7.2 Hz), 1.25 (m, 14H), 1.58 (m, 4H), 2.33 (t, 2H, J =7.7 Hz), 3.22 (q, 4H, J =7.2 Hz), 3.64 (m, 2H), 4.61 (br t, 1H), 5.93 (dd, 1H, J =7.4 Hz, 4.8 Hz), 6.61 (s, 1H) and 7.64 (s, 1H).

$^{13}$CNMR(CDCl$_3$) 2.8, 6.9, 13.5, 13.8, 22.4, 24.8, 28.9, 29.0, 29.1, 29.2, 29.4, 31.7, 34.3, 41.1, 44.8, 68.1, 119.6, 122.6, 144.8, 157.2, 159.9 and 173.9. HRMS exact mass calculated for C$_{29}$H$_{54}$N$_2$O$_4$Si (M+) 522.3853, found 522.3859.

4-[1-Dodecanoyloxy-2-(N',N'-diethyl)carboxyamido]ethyl-(5-hydroxy-2(5H)-furanone (Compound 30)

A mixture of 4-[1-dodecanoyloxy-2-(N',N'-diethyl)amido]ethyl-2-triethylsilylfuran (Compound 29, 39.5 mg, 0.07 mmol), water (a few drops) and Rose Bengal (5 mg) in acetone (6 ml) was exposed to singlet oxygen at 0° for 2 hours. The residue, after solvent removal, was purified by a silica column using 10% methanol/chloroform to give the title furanone.

$^1$HNMR(CDCl$_3$) 0.79 (t, 3H, J =6.2 Hz), 1.18 (m, 16H), 1.56 (t, 2H, J =7.3 Hz), 1.74 (p, 2H, J =7.5 Hz), 2.13 (t, 2H, J =7.5 Hz), 2.19 (t, 2H, J =7.5 Hz), 2.55 (t, 1H), 3.50 (br m, 2H), 5.64 (br, 1H), 5.99 (br, 1H) and 6.11 (br, 1H).

$^{13}$CNMR(CDCl$_3$) 14.4, 22.3, 23.7, 25.8, 30.2, 20.4, 30.5, 30.6, 30.8, 33.1, 34.1, 34.8, 35.9, 41.9, 70.0, 100.0, 120.4, 166.3, 171.9, 174.0 and 176.0.

FURTHER SPECIFIC EXAMPLES

Example 11

As in Example 5 (preparation of Compound 16) but substituting acetic anhydride with phenyl isocyanate and carrying through the reaction sequence gives 4-[(1-phenylcarbamoyl-2-dodecanesulfonylamido)ethyl]-5-hydroxy-2(5H)-furanone (Compound 31).

Example 12

As in Example 5 (preparation of Compound 16) but substituting acetic anhydride with dodecanoyl chloride and carrying through the reaction sequence gives 4-[(1-dodecanoyloxy-2-dodecanesulfonylamido)ethyl]-5-hydroxy-2(5H)-furanone (Compound 32).

Example 13

Reacting 4-(2-amino-1-hydroxy)ethyl-2-triethylsilylfuran (Compound 7) with dodecyl chloroformate gives 4-[1-hydroxy-2-N-(carbododecyloxy)amino]ethyl-2-triethylsilylfuran (Compound 33). Acetylating this intermediate with acetic anhydride gives 4-[1-acetoxy-2-N-carbododecyloxy)amino]ethyl-2-triethylsilylfuran. Oxidizing this acetate with singlet oxygen, as in preparation of Compound 10, gives 4-(1-acetoxy-2-N-carbododecyloxy)amino]ethyl-5-hydroxy-2(5H)-furano (Compound 34).

Example 14

As in Example 13 (preparation of Compound 34) but substituting acetic anhydride with phenyl isocyanate and carrying through the reaction sequence gives 4-[1-phenylcarbamoyl-2-N-carbododecyloxy)amino]ethyl-5-hydroxy-2(5H)-furanone (Compound 35).

Example 15

Reacting 4-(2-amino-1-hydroxy)ethyl-2-triethylsilylfuran (Compound 7) with dodecyl isocyanate and oxidizing the intermediate with singlet oxygen gives 4-[(1-hydroxy-2-dodecyluredo)]ethyl-5-hydroxy-2(5H)-furanone (Compound 36).

Example 16

As in Example 15 (preparation of Compound 36) but acetyl the intermediate with ethyl chloroformate before oxidizing with singlet oxygen gives 4-(1-ethyoxycarbonyloxy-2-dodecylureido)ethyl-5-hydroxy-2(5H)-furanone (Compound 37).

Example 17

Reacting 4-[1-hydroxy-2-(3-carboxypropaneamido)-]ethyl-2-triethylsilylfuran Compound 18 (from Example 6) with glutaric anhydride and oxidizing the product with singlet oxygen gives 4-(1-glutaryloxy-2-(3-carboxypopaneamido)]ethyl-5-hydroxy-2(5H)-furanone (Compound 38).

Example 18

As in Example 17 (preparation of Compound 38) but substituting glutaric anhydride with phenyl isocyanate and carrying through the reaction sequence to give 4-[1-phenylcarbamoyl-2-(3-carboxypropaneamido)]ethyl-5-hydroxy-2(5H)-furanone (Compound 39).

Example 19

As in Example B (preparation of Compound 22) but substituting acetic anhydride with dodecanoyl dichloride and carrying through the reaction sequence gives 4-[1-(10-carboxyundecanoyloxy)-2-(10-carboxydecaneamido)]ethyl-5-hydroxy-2(5H)-furanone (Compound 40).

Example 20

Reacting 4-(2-amino-1-hydroxy)ethyl-2-triethylsilylfuran (Compound 7) with methanesulfonyl chloride gives 4-(1-hydroxy-2-methanesulfonylamido)ethyl-4-triethylsilylfuran (Compound 41). Coupling this intermediate to dodecanoyl dichloride and oxidizing the product with singlet oxygen gives 4-[1-(10-carboxyundecanoyloxy)-2-methanesulfonylamido]ethyl-5-hydroxy-2(5H)-furanone (Compound 42).

Example 21

Reacting 4-(2-amino-1-hydroxy)ethyl-2-triethylsilylfuran (Compound 7) with phosgene and N-methyl-piperazine gives, as in preparation of Compound 25, 4-[1-hydroxy-2-(N'-methylpiperazine)carboamido]ethyl-2-triethylsilylfuran (Compound 43). Treatment of the intermediate with dodecanoyl chloride and oxidizing the intermediate with singlet oxygen gives 4-[1-dodecanoyloxy-2-(N'-methylpiperazine)carboamido]ethyl-5-hydroxy-2(5H)-furanone (Compound 44).

Example 22

As in Example 21 (preparation of Compound 44) but substituting N-methylpiperazine with morpholine and carry through the reaction sequence to give 4-[1-dodecanoyloxy-2-(morpholine)carboamido]ethyl-5-hydroxy-2(5H)-furanone (Compound 45).

Example 23

Reacting 4-(2-amino-1-hydroxy)ethyl-2-triethylsilylfuran (Compound 7) with 4-(N,N-dimethylamino)-1-butyric acid, diyclohexylcarbodiimide and 4-dimethylaminopyridine gives 4-[1-hydroxy- 2-(4-N,N-dimethylamino)propylcarboxyamido]ethyl-2-triethylsilylfuran (Compound 46). Treatment of this intermediate with dodecanoyl chloride and oxidizing this intermediate with singlet oxygen gives 4-[dodecanoyloxy-2-(4-N,N-dimethylamino)propylcarboamido]ethyl-5-hydroxy-2(5H)-furanone (Compound 47).

Example 24

As in Example 23 (preparation of Compound 47) but substituting 4-(N,N-dimethylamino)-1-butyric acid with benzene-1,3,5-tricarboxylic acid and carry through the reaction sequence gives 4-[1-dodecanoyloxy-2-(3,5-dicarboxyphenyl)carboamido]ethyl-5-hydroxy-2(5H)-furanone (Compound 48).

Example 25

As in Example 23 (preparation of Compound 47) but substituting 4-(N,N-dimethylamino)-1-butyric acid with 1,2,4-benzenecarboxylic acid anhydride and carry through the reaction sequence gives 4-[1-dodecanoyloxy-2(3,4-dicarboxyphenyl)carboamido]ethyl-5-hydroxy-2(5H)-furanone (Compound 49).

Example 26

. Reacting 4-(2-amino-1-hydroxy)ethyl-2-triethylsilylfuran (Compound 7) with methyl methylphosphonochloridate gives 4-[1-hydroxy-N-(MeP(0)Me)amino]ethyl-2-triethylsilylfuran (Compound 50). Treatment of this intermediate with dodecanoyl chloride and oxidizing the product with singlet oxygen gives 4-[1-dodecanoyloxy-N-(MeP(0)Ome(amino]ethyl-5-hydroxy-2(5H)-furanone (Compound 51).

In the above-described phospholipase $A_2$ assay the compounds of the invention were found to provide 50% inhibition ($IC_{50}$) of bee venom phospholipase $A_2$ at the following concentrations (in micromoles), as indicated in Table 1.

TABLE 1

| Phospholipase $A_2$ Assay | |
|---|---|
| Compound name of number | $IC_{50}$ (um) |
| 1* | 0.03 |
| 17 | 0.03 |
| 12 | 0.04 |
| 13 | 0.03 |
| 23 | 0.09 |
| 28 | 0.05 |
| 30 | 0.02 |
| 10 | 0.28 |

*Data for Compound 1 (monoalide) are provided for comparison.

What is claimed is:

1. Compounds of the formula

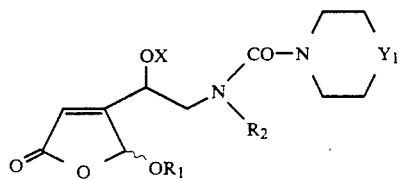

where
- $R_1$ is H or alkyl of 1 to 20 carbons, $CO-R_1^*$, $CO-O-R_1^*$, $CO-NH-R_1^*$, or $PO(OR_1^*)_2$, $PO(OR_1^*)R_1^*$ where $R_1^*$ independently is H, alkyl of 1 to 20 carbons, or phenyl;
- $R_2$ is H or alkyl of 1 to 20 carbons;
- X is H, $R_3$, $CO-R_3$, $CO-O-R_3$, $CO-NH-R_3$, $CO-N-(R_3)_2$, $PO(OR_3)_2$, $PO(OR_3)R_3$, and $R_3$ independently is H, phenyl, alkyl of 1 to 20 carbons or is alkyl of 1 to 20 carbons substituted with a hydroxyl, alkoxy, amino, thioalkoxy or with a $COR_3^*$ group where $R_3^*$ is H, lower alkyl, OH, $OR_3^{}$, $NH_2$, $NHR_3^{}$ or $N(R_3^{})_2$ group where $R_3^{}$ independently is H or lower alkyl, with the proviso that when X is $R_3$, $CO-O-R_3$ or is $CO-NH-R_3$ then $R_3$ is not hydrogen;
- $Y_1$ is O, NH, N-methyl or $N-SO_2$-methyl, and salts of said compounds.

2. The compounds of claim 1 where $R_1$ is H.
3. The compounds of claim 1 wherein $R_2$ is hydrogen.
4. The compounds of claim 1 where X is H.
5. The compounds of claim 1 where X is $R_3-CO$.
6. The compounds of claim 1 where X is $CO-O-R_3$.
7. The compounds of claim 1 where X is $CO-NH-R_3$.
8. Compounds of the formula

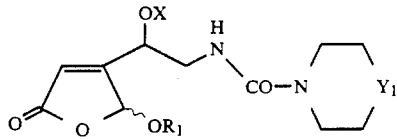

where
- $R_1$ is H or alkyl of 1 to 20 carbons, $CO-R_1^*$, $CO-O-R_1^*$, $CO-NH-R_1^*$, or $PO(OR_1^*)_2$, $PO(OR_1^*)R_1^*$ where $R_1^*$ independently is H, alkyl of 1 to 20 carbons, or phenyl;
- X is H, $R_3$, $CO-R_3$, $CO-O-R_3$, $CO-NH-R_3$, or $CO-N-(R_3)_2$, and $R_3$ independently is H, phenyl, alkyl of 1 to 20 carbons or is alkyl of 1 to 20 carbons substituted with a $COR_3^*$ group where $R_3^*$ is OH, $OR_3^{}$, $NH_2$, $NHR_3^{}$ or $N(R_3^{})_2$ group where $R_3^{}$ independently is H or lower alkyl, with the proviso that when X is $R_3$, $CO-O-R_3$ or is $CO-NH-R_3$ then $R_3$ is not hydrogen;
- $Y_1$ is O, NH, N-methyl or $N-SO_2$-methyl, and salts of said compounds.

9. The compounds of claim 8 where $y_1$ is $N-SO_2$-methyl.
10. The compounds of claim 9 where X is $CO-R_3$ and $R_3$ is alkyl.
11. The compounds of claim 10 where $R_3$ is $CH_3-(CH_2)_{10}-$.
12. The compound of claim 11 where $R_1$ is H.
13. A pharmaceutical composition comprising one or more compounds set forth in claim 1, including a pharmaceutically acceptable carrier.

* * * * *

UNITED STATES PATENT AND TRADEMARK OFFICE
CERTIFICATE OF CORRECTION

PATENT NO. : 5,212,172
DATED : May 18, 1993
INVENTOR(S) : Gary C. M. Lee

Page 1 of 4

It is certified that error appears in the above-identified patent and that said Letters Patent is hereby corrected as shown below:

Column 2, line 41, "perazinyl" should be —piperazinyl—;
Column 7, line 46, after "Fura-2" add —.—;
Column 9, line 23 "trielsilyl" should be —triethysilyl—;
Column 9, line 27, after "U.S.: add —Letters—;
Column 10, line 22 "trialxylsilyl" should be —trialkylsilyl—;
Column 13, line 12, after "Formula" add —5—;
Column 13, line 15, "Schemes to" should be —schemes, to—;
Column 16, line 45, "hexane:" should be —hexane;—;
Column 16, line 62, "triethlsily" should be —triethylsily—;
Column 16, line 67, "(CDC13)" should be —(CDCl$_3$)—;
Column 17, line 7, "2.07" should be —20.7—;
Column 17, line 22, before "0.73" add —:—;
Column 17, line 34, "1.6B" should be —1.68—;
Column 17, line 48, after "(Compound 9)" add —:—;
Column 17, line 59, after "(Compound 8)" add —:—;
Column 17, line 61, after "(CDCl$_3$)" add —:—;
Column 18, line 5, "(Compound s)" should be —(Compound 8)—;
Column 18, line 11, "(CD3OD)" should be —(CD$_3$OD)—;
Column 18, line 30, before "0.77" insert —:—;
Column 18, line 32, "(t 2H J = 7.9 Hz) 3.70(m 2H)" should be —(t, 2H, J = 7.9 Hz) 3.70(m, 2H)—;

UNITED STATES PATENT AND TRADEMARK OFFICE
CERTIFICATE OF CORRECTION

PATENT NO. : 5,212,172
DATED : May 18, 1993
INVENTOR(S) : Gary C. M. Lee

It is certified that error appears in the above-identified patent and that said Letters Patent is hereby corrected as shown below:

Column 18, line 41, "Water" should be —water—;

Column 19, line 1, "(br,s," should be —(br, s,—;

Column 19, line 5, "M+" should be —$M_n^+$—;

Column 19, line 25, "26" should be —1.26—;

Column 19, line 26, "2H) 1.81 (m 2H)," should be —2H), 1.81 (m, 2H), —;

Column 19, line 27, "(m 1H)" should be —(m, 1H)—;

Column 19, line 33, "dodecanesulfonylamide" should be —dodecanesulfonylamido—;

Column 19, line 41, after "methanol" insert —/—;

Column 20, line 4, "idodecane..." should be —dodecane...—;

Column 20, line 10, "0o" should be —0°—;

Column 20, line 13, after "(CDCl$_3$)" insert —:—;

Column 20, line 26, "lethyl" should be —]ethyl—;

Column 20, line 38, after "(CDCl$_3$)" add —:—;

Column 20, line 49, "lethyl" should be —]ethyl—;

Column 20, line 54, "0.3" shoould be —0.39 —;

Column 21, line 9, "lethyl" should be —]ethyl—;

Column 21, line 28, before "3.1" insert —:—;

Column 21, line 30, "Calculated" should be —calculated—;

Column 21, line 31, "453,2913" should be —453.2913—;

Column 21, line 38, "0o" should be —0°—;

Column 21, line 33, "lethyl" should be —]ethyl—;

UNITED STATES PATENT AND TRADEMARK OFFICE
CERTIFICATE OF CORRECTION

PATENT NO. : 5,212,172

DATED : May 18, 1993

INVENTOR(S) : Gary C. M. Lee

It is certified that error appears in the above-identified patent and that said Letters Patent is hereby corrected as shown below:

Column 21, line 48, "(CD3OD)" should be —($CD_3OD$)"—;

Column 21, line 52, "lethyl" should be —]ethyl—;

Column 21, line 62, before "1.29" add —:—;

Column 21, line 67, "M+" should be —$M^+$—;

Column 22, line 2, "lethyl" should be —]ethyl—;

Column 22, line 20, before "2.9" add —:—;

Column 22, line 26, "lethyl" should be —]ethyl—;

Column 22, line 37, before "1.26" add —:—;

Column 22, line 59, "164$M^{30}$" should be —164$M^+$—;

Column 22, line 63, "lethyl" should be —]ethyl—;

Column 23, line 38, "amidolethyl" should be —amido]ethyl—;

Column 23, line 62, "Dodecaneyloxy" should be —Dodecanoyloxy—;

Column 23, line 63, "amidolethyl"should be —amido]ethyl—;

Column 24, line 17, "Dodecaneyloxy" should be —Dodecanoyloxy—;

Column 24, line 17, "amidolethyl" should be —amido]ehtyl—;

Column 24, line 27, before "magnesium" insert —(—;

Column 24, line 36, before "2.8" add —:—;

Column 24, line 53, before "0.79" add—:—;

UNITED STATES PATENT AND TRADEMARK OFFICE
CERTIFICATE OF CORRECTION

PATENT NO. : 5,212,172
DATED : May 18, 1993
INVENTOR(S) : Gary C. M. Lee

It is certified that error appears in the above-identified patent and that said Letters Patent is hereby corrected as shown below:

Column 24, line 58, "20.4" should be —30.4—;

Column 25, line 37, "acetyl" should be —acetylating—;

Column 25, line 58, "B" should be —8—;

Column 26, line 62, "Ome" should be —OMe—.

Signed and Sealed this

First Day of March, 1994

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,212,172

DATED : May 18, 1993

INVENTOR(S) : Gary C. M. Lee

It is certified that error appears in the above-identified patent and that said Letters Patent is hereby corrected as shown below:

In the abstract, line 26, from bottom, "O-COR$_4^*$ group should be —O—COR$_4^*$ group—;

Column 1, line 64, delete one "of";

Column 10, line 34, "carboxamide." should be —carboxamide,—;

Column 19, line 56, "dodecansulfonylamido" should be —dodecanesulfonylamido—.

Signed and Sealed this

Third Day of May, 1994

Attest:

BRUCE LEHMAN

Attesting Officer

Commissioner of Patents and Trademarks